(12) United States Patent
King et al.

(10) Patent No.: US 7,157,051 B2
(45) Date of Patent: Jan. 2, 2007

(54) SAMPLING MANAGEMENT FOR A PROCESS ANALYSIS TOOL TO MINIMIZE SAMPLE USAGE AND DECREASE SAMPLING TIME

(75) Inventors: Mackenzie E. King, Southbury, CT (US); Thomas Chatterton, Cedar Park, TX (US); Richard Bhella, Gilbert, AZ (US)

(73) Assignee: Advanced Technology Materials, Inc., Danbury, CT (US)

( * ) Notice: Subject to any disclaimer, the term of this patent is extended or adjusted under 35 U.S.C. 154(b) by 146 days.

(21) Appl. No.: 10/658,948

(22) Filed: Sep. 10, 2003

(65) Prior Publication Data

US 2005/0053522 A1 Mar. 10, 2005

(51) Int. Cl.
*G01N 31/00* (2006.01)
(52) U.S. Cl. ............... 422/68.1; 422/81; 422/82.01; 422/82.05; 422/99; 422/100; 422/103
(58) Field of Classification Search ............... 422/50, 422/68.1, 70, 81, 82.01, 82.05, 99, 100, 103
See application file for complete search history.

(56) References Cited

U.S. PATENT DOCUMENTS

| 4,326,940 | A | * | 4/1982 | Eckles et al. | ............... 204/232 |
| 5,106,413 | A | * | 4/1992 | Takehawa | ............... 106/1.22 |
| 6,495,011 | B1 | | 12/2002 | Robertson | |
| 6,592,737 | B1 | | 7/2003 | Robertson | |

\* cited by examiner

*Primary Examiner*—Jill Warden
*Assistant Examiner*—Sam P. Siefke
(74) *Attorney, Agent, or Firm*—Steven J. Hultquist; Intellectual Property/Technology Law; Margaret Chappuis

(57) ABSTRACT

A method and system for analysis of additives in electrolysis plating solutions, using a flow management system that minimizes loss of plating solutions and decreases sampling time. The system includes at least one analysis chamber, a sampling duct connected to processing tool, a four-way valve positioned between the processing tool and the sampling duct, at least one carrier fluid duct connected to the analysis chamber, at least one actuatable multi-port valve that provides a transference platform between the sampling duct and the at least one carrier fluid duct, and a flow sensor connected to the sampling duct and positioned downstream from the at least one actuatable multi-port valve.

28 Claims, 6 Drawing Sheets

SAMPLING MANAGEMENT FOR A PROCESS ANALYSIS TOOL TO MINIMIZE SAMPLE USAGE AND DECREASE SAMPLING TIME

BACKGROUND OF THE INVENTION

1. Field of the Invention

The present invention relates generally to the determination of additives in metal plating solutions, and more specifically, to a method and system for analysis of additives in electrochemical plating solutions using a flow management system that minimizes loss of plating solutions and decreases sampling time.

2. Description of the Related Art

The microelectronic manufacturing industry applies a wide range of thin film materials to form microelectronic structures. These thin film materials include metals and metal alloys such as, for example, nickel, tungsten, tantalum, solder platinum, copper, copper-zinc, as well as dielectric materials, including metal oxides, semiconductor oxides, and perovskite materials.

A wide range of processing techniques has been used to deposit such thin films, including chemical vapor deposition, electroplating and electroless plating. Of these techniques, electrochemical processing techniques, i.e., electroplating, and electroless plating are the most economical.

Electroless plating uses an electrolyte wherein suitable salts of the desired deposition metals are dissolved therein. The electrolyte can be water-based, organic-based or a molten salt, depending on the specific metal to be deposited.

Metal deposition from solution has been used for depositing copper during the production process of printed circuit boards in the microelectronics industry. Electrochemical deposition is the preferred method because of several advantages over chemical or physical vapor deposition that include the avoidance of using a vacuum system and overall reduced costs. However, when electrochemical techniques are employed, optimum process performance cannot be obtained without careful control of the plating bath chemistry. Notably, the quality and efficiency of the electrochemical plating process depend on the bath composition, pH and temperature.

Currently, most semiconductor manufacturers replenish plating baths based on time or energy consumption (e.g., amp hours). However, the use of such replenishment methods is based on the fact that the plating system always functions under ideal conditions, when in fact, human error and system malfunctions can affect the depletion rate of the components. To overcome the uncertainty of timed replenishing operations, in-line monitoring systems have been adapted for use in plating systems that monitor the metal levels in the plating baths and replenish the baths when needed. These systems minimize contamination, however, the sampling process can be time-consuming and any delay in determining analyte concentrations in the solutions can produce problems in maintaining the desired properties of the electrodeposited metals. Furthermore, these in-line sampling techniques can consume a considerable amount of sample thereby wasting expensive plating solutions and/or adversely affecting the economics of the semiconductor manufacturing operation.

Accordingly, there is a need in the art for a sampling method and system that overcome the shortcomings of the prior art, such as excessive wastage of plating solutions, slow reaction times from sampling to replenishing of plating baths, and contamination from previous testing samples.

SUMMARY OF THE INVENTION

The present invention relates to a method and system for monitoring the concentration of components in a plating bath solution.

In one aspect, the present invention relates to a method for sample analysis that minimizes sampling time of a plating bath sample while reducing cross-contamination between samples.

In another aspect, the present invention relates to a sampling system that accurately transfers a larger sample to the analysis system thereby reducing sampling time.

In yet another aspect, the present invention relates to a sampling system for determining concentration of additives in a metal plating bath from an electrochemical processing tool, the system comprising:
 a) at least one analysis chamber;
 b) a sampling duct comprising a sampling inlet and at least one sample loop, wherein the sampling inlet is in fluid communication with the electrochemical processing tool for receiving a plating bath sample for analysis in the at least one analysis chamber;
 c) a four-way valve positioned between the sampling inlet and the electrochemical processing tool, wherein the plating bath sample is flowed through the four-way valve from the electrochemical processing tool into the sampling duct;
 d) at least one actuatable multi-port valve in fluid communication with the sampling duct;
 e) at least one carrier fluid duct in fluid communication with the analysis chamber, wherein the carrier fluid duct and sampling duct are in fluid communication via the actuatable multi-port valve;
 f) a flow sensor in fluid communication with the sampling duct and positioned downstream from the at least one actuatable multi-port valve, wherein the flow sensor measures a predetermined quantity of plating bath sample flowing through sample duct;
 g) a purging gas source in fluid communication with the four-way valve for introducing a purging gas source into the sampling duct between successive sample analyses; and
 h) a waste line in fluid communication with the four-way valve, wherein plating bath solution can be transferred from the processing tool through the four way valve to the waste line.

In yet another aspect, the present invention relates to a sampling system for determining concentrations of additives in a metal plating bath from a processing tool, the system comprising:
 a) at least one analysis chamber;
 b) a sampling duct comprising a sampling inlet and at least one sample loop positioned upstream from the sample inlet, wherein the sampling duct is in fluid communication with the processing tool for receiving a plating bath sample for analysis in the at least one analysis chamber;
 c) an inlet four way valve positioned between the sampling inlet and the processing tool, wherein the inlet four-way valve is in fluid communication with the sample inlet, and wherein the plating bath sample is flowed through the inlet four-way valve from the processing tool into the sampling duct;
 d) at least one carrier fluid duct in fluid communication with the analysis chamber and sampling duct;
 e) at least one actuatable multi-port valve in fluid communication with the sampling duct and carrier fluid duct, wherein the at least one actuatable multi-port valve has a first and second position, and wherein the first position provides a flow path for flowing the plating bath sample through the sampling duct and the second position provides a flow path for flowing the plating bath sample from the sampling duct to the carrier fluid duct;

f) a flow sensor in fluid communication with the sampling duct and positioned downstream from the at least one actuatable multi-port valve, wherein the flow sensor measures a predetermined quantity of plating bath sample flowing through sample duct and then triggers the actuation of the multi-port valve into the second position;

g) a purging gas source in fluid communication with the four-way valve for introducing a purging gas source into the sampling duct to purge previous plating bath sample from the system;

h) a waste line in fluid communication with the four-way valve, wherein plating bath solution is transferred from the processing tool through the four way valve to the waste line;

i) a valve control system for controlling the inlet four-way valve to provide a first mode in which the plating bath sample is flowed from the processing tool into the sample duct, a second mode in which the plating bath sample from the processing tool is directed to the waste line, a third mode in which the purge gas source is introduced to the sample duct to purge plating bath sample from the sample duct, and a fourth mode in which the purging gas source is directed to the waste line.

A still further aspect of the present invention relates to a liquid transferring system for inclusion in the sampling system of the present invention comprising:

a) a cylindrical housing sized to transfer at least 10 ml of liquid, wherein the cylindrical housing has an open first end and a closed second end;

b) a cylindrical plunger rod having a first and second end and slidably mounted within the cylindrical housing, wherein the second end of the plunger rod extends through the closed second end of the housing;

c) a tip comprising a body portion having a first and second tip end and a central bore therethrough wherein the first end of the tip is connected to the first end of the cylindrical housing, and wherein the second end has a bore diameter sized to reduce back pressure when filling and reduce the formation of irreproducible droplets at the second end of the tip; and d) a flexible sealing member connected to the first end of the plunger rod, wherein the flexible sealing member comprises three overlapping radial flaps to form a sealed chamber between the flexible sealing member and the second end of the tip, and wherein the sealed chamber holds a transferable liquid.

In yet another aspect, the present invention relates to a method for analyzing an analyte in a plating bath sample from an electrochemical deposition solution, the method comprising:

a) providing an analysis system comprising at least one analysis chamber, a sampling duct connected to an electrochemical processing tool, a four-way valve positioned between the electrochemical processing tool and the sampling duct, at least one carrier fluid duct connected to the analysis chamber, at least one actuatable multi-port valve that provides a transference platform between the sampling duct and the at least one carrier fluid duct, and a flow sensor connected to the sampling duct and positioned downstream from the at least one actuatable multi-port valve;

b) flowing a sufficient amount of a plating bath sample from the electrochemical processing tool through the four-way valve into the sampling duct;

c) stopping the flow of the plating bath sample from the electrochemical processing tool when the flow sensor senses a sufficient amount of sample for testing in the analysis chamber; and d) actuating the multi-port valve to transfer a predetermined amount of the plating bath sample from the sample duct to the carrier fluid duct for transference into the analysis chamber for analysis therein.

Other aspects and features of the invention will be more fully apparent from the ensuing disclosure and appended claims.

DETAILED DESCRIPTION OF THE INVENTION AND PREFERRED EMBODIMENTS THEREOF

The present invention provides a sampling system for determining analytes in a metal plating bath sample. The system is arranged for the analysis of one sample in an analysis chamber while a sample loop is being refilled for the next sample analysis. Further, the sampling system of the present invention provides for sequential analysis of a plating bath solution that requires different sample volumes and different reagents. Still further, the sampling system of the present invention reduces the use of multiple three-way valves and ensures that cross-contamination between samples is reduced because an old sample is purged from the system before a new sample is introduced for analysis.

Figure 1:
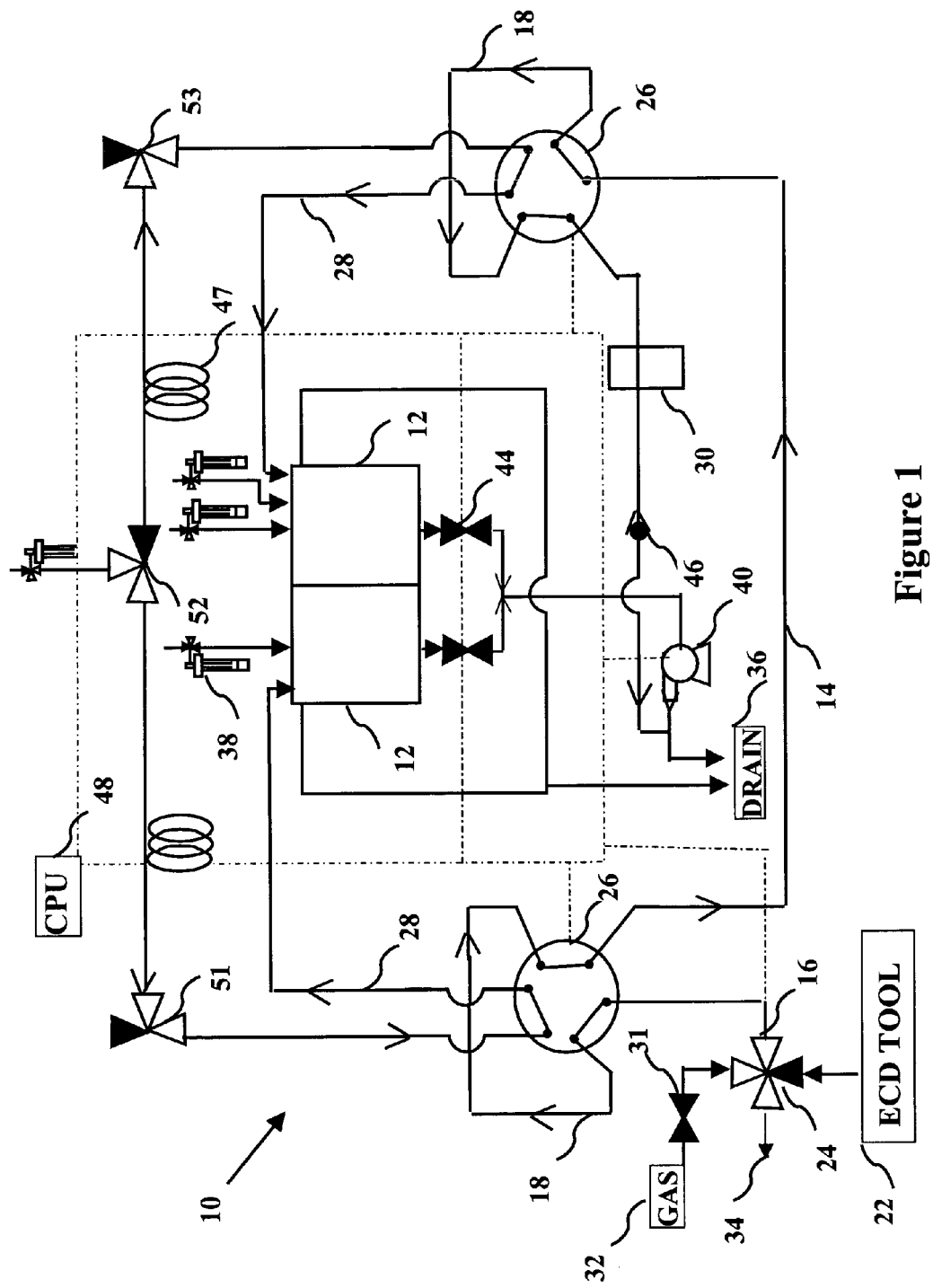
FIG. 1 illustrates one embodiment of the present invention for analysis of organic components in a plating bath solution

Referring first to FIG. 1 of the drawings, the reference 10 generally denotes a sampling system of the present invention used to measure organic component concentrations added to an electrochemical deposition bath to control the uniformity of film thickness across a wafer surface. The sampling system includes at least one analysis chamber 12, a sampling duct 14 which includes a single sample inlet port 16 and at least one sample loop 18. The system further comprises a four-way valve 24 positioned between the sample inlet port 16 and an electrochemical processing tool 22 to provide a flow path for the plating bath solution that is drawn from the processing tool 22 into the sampling duct 14.

The sampling system further comprises at least one actuatable six-port valve 26 that provides for routing of the plating bath sample through multiple ducts. In a first position, the valve is positioned so that the plating bath sample flows through the sampling duct 14 and fills the sample loops 18. In a second position, the plating bath sample that is contained in the sample loop is diverted to the analysis chamber 12 via carrier duct 28. A flow sensor 30 is positioned in the sample duct 14 down stream from sample loops 18 and multi-port valves 26 and positioned upstream from the drain outlet 36. The flow sensor is responsive to a predetermined quantity of the plating bath sample flowing past the sensor, to terminate flow intake of plating bath solution from the electrochemical processing tool. The system is controlled and monitored by a suitable computer 48 with capabilities to control the various valves, pumps, etc., as described below. Suitable computer software is commercially available to automatically perform the controlling functions to coordinate actuation of various valves.

In use, the present sampling system draws in a sufficient amount of a sample of the plating bath solution from the electrochemical processing tool 22 to rinse from the sample duct 14 and sample loops 18 any remaining sample solution from the previous sample analysis and/or any purging gas from the system. Notably, prior to filing the sample duct and sample loops with a plating bath sample, the system can be purged with a purging gas source 32 introduced into the sampling system via the four-way valve 24. Any gas source that is inert may be used in the present system including, but not limited to, nitrogen, hydrogen and carbon dioxide. During the purging and filling process, the plating bath sample may be drawn through the sampling duct 14 to drain outlet 36 by a pumping system, for example, drain pump 40 or the plating bath sample may flow into the sampling system under its own pressure. Typically, from 20 to 1000 microliters of the plating bath solution are drawn through the system to ensure complete removal of any previous sampling solution.

In operation, the four-way valve 24 has multiple modes for transference of fluid from the processing tool 22 or the gas source 32 through the sampling system. The inlet four-way valve provides a first mode in which the plating bath sample is flowed from the processing tool into the sample duct 14, a second mode in which the plating bath sample from the processing tool is directed to the waste line 34, a third mode in which the purge gas source is introduced to the sample duct to purge plating bath sample from the sample duct, and a fourth mode in which the purging gas source is directed to the waste line.

Thus, when the four-way valve is in the first mode, the plating bath sample is drawn from the processing tool into the sample duct 14 through the first and second sample loops 18, passing through the sensors of the flow sensor 30 and the surplus sample solution passes to drain 36, thereby flushing the system between the four-way valve 24 and drain 36.

Figure 3:
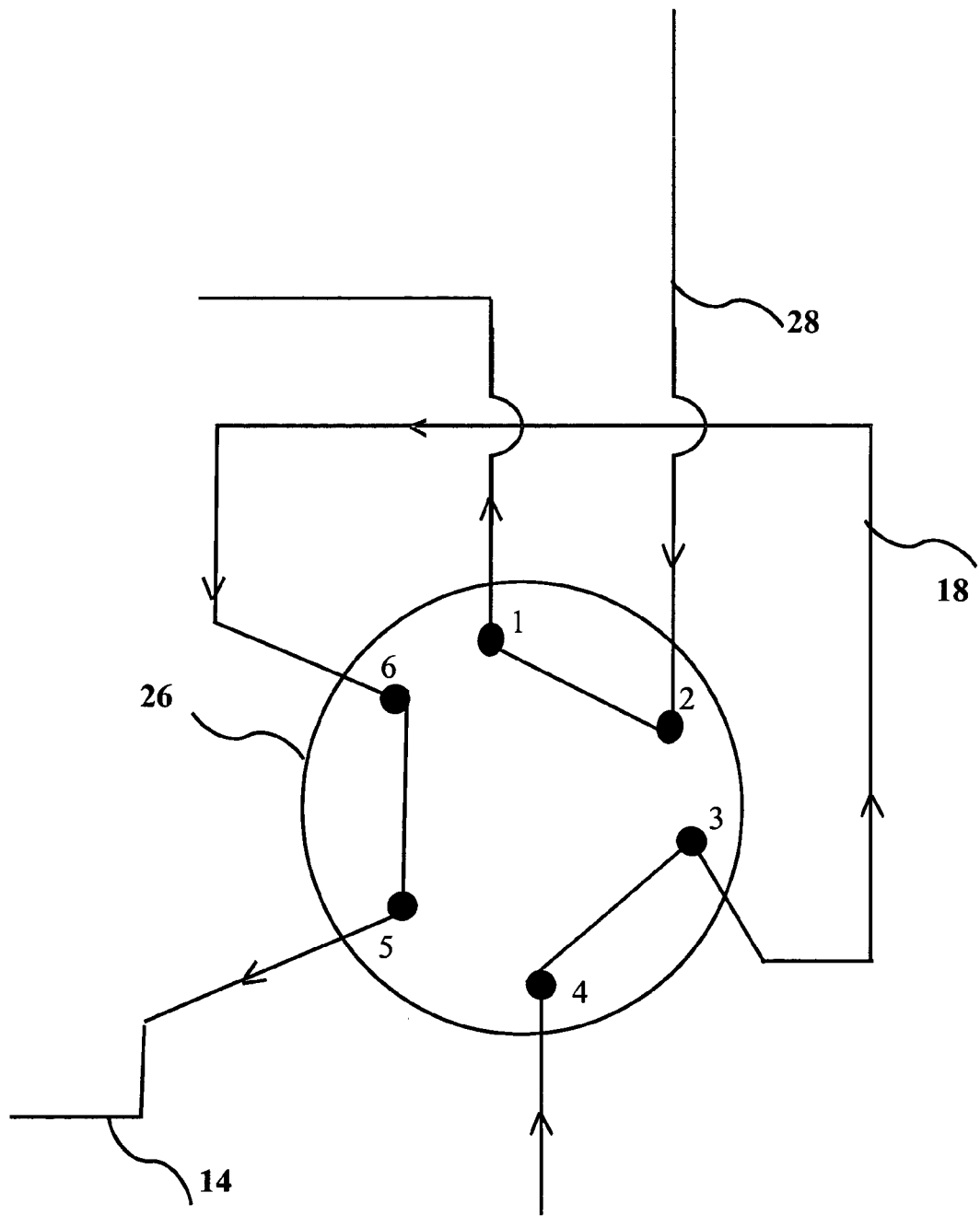
FIG. 3 illustrates a multi-port valve (six (6) ports) as used in the present invention in the loading position of the sample loop.
Figure 4:
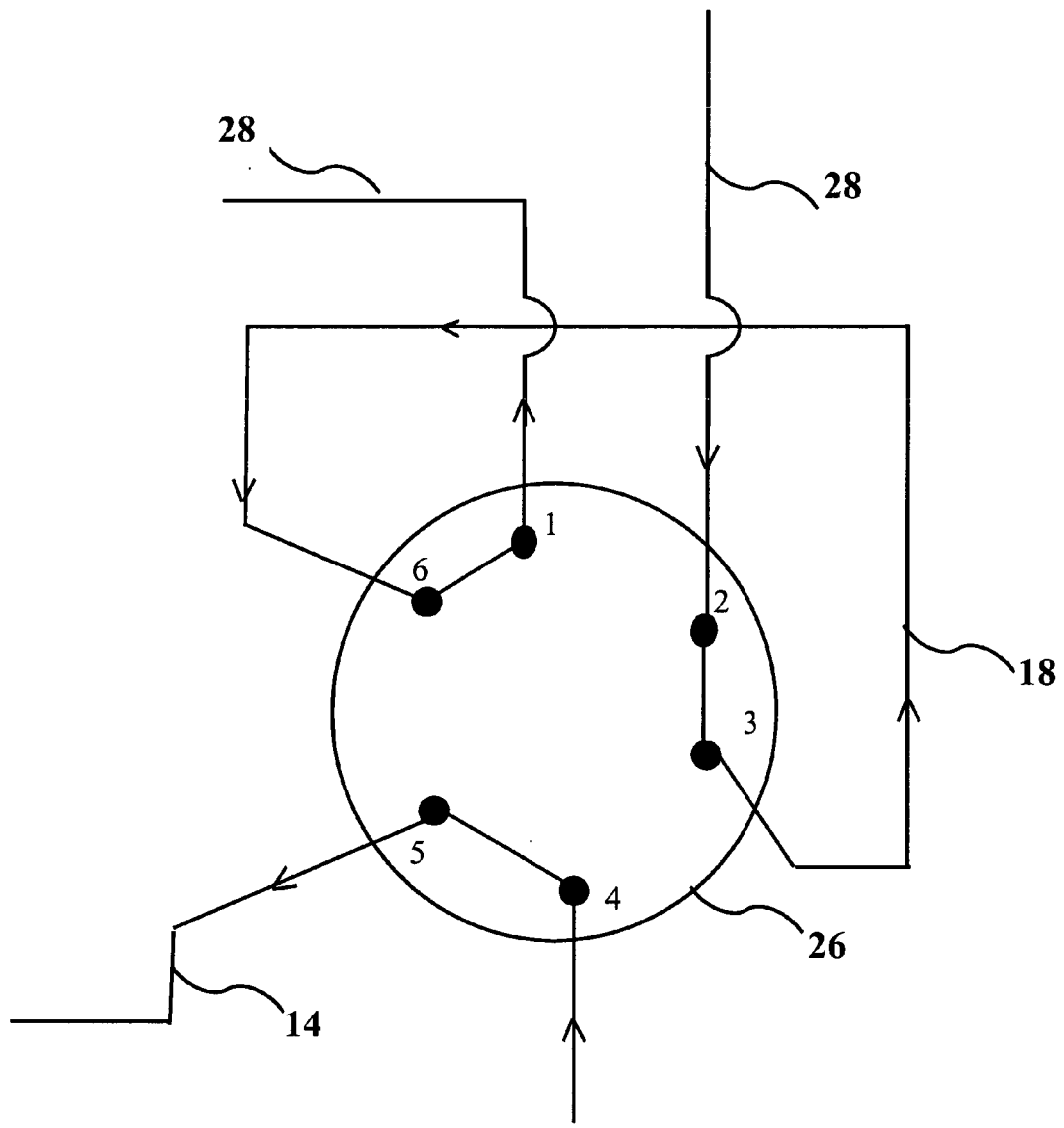
FIG. 4 illustrates the multi-port valve of FIG. 3 in the transferal position of the plating bath sample from the sample loop to the carrier duct.

The multi-port valves 26 have two positions for directing the sample into multiple ducts as shown in FIGS. 3 and 4. The first position, as shown in FIG. 3, provides the flow path of the plating bath sample as it flows through ports 4 and 3 and into the sample loop. The sample loop fills with the sample solution, which then flows through ports 6 and 5 and past the flow sensor to the drain outlet 36. Thus, the first position provides for the plating bath sample to flow through the sampling duct 14 to fill the sample loops 18 and pass into the drain outport. FIG. 4 illustrates the second position of the actuatable six-port valve and the flow path of the plating bath sample as it is moved from the sample loop by the carrier fluid into the carrier fluid duct. As the valve is actuated into the second position, ports 2 and 3 are connected thereby providing a flow path for the sample solution in the sample loop 18 to flow through ports 6 and 1 and into the carrier fluid duct 28 to the analysis chamber. Thus, the second position provides for flowing the plating bath sample from the sampling loops 18 to the carrier fluid ducts 28 for transference into the analysis chamber 12. The use and connection setup of the described six-port valves are within the skill of the art, based on the disclosure herein, and any commercially available model may be used in the present system.

Flow sensor 30 is positioned in the sampling duct to sense movement of the plating bath sample as it initially flows through the sensed area of the sample duct. Preferably, the flow sensor is programmed to sense flow for a predetermined amount of time, which is sufficient to rinse the system and to ensure that the flow in the sample duct is consistent. Any commercially available flow sensor that monitors the flow of the liquid through the sampling duct may be used in the present system including, but not limited to, optical, ultrasonic, magnetic, electromagnetic, and inline flow sensors.

After a predetermined time period of sensed flow, the computer operated system turns off the drain pump and inactivates the four-way valve 24 thereby retaining the sample in the sample duct and preventing any additional sample from entering the sample duct. The multi-port valves 26 are switched from the first position to the second position thereby allowing the sample in the sample loops 18 to be redirected to the carrier fluid ducts 28 for transference to the analysis chambers 12.

Multiple reagent reservoirs 38 are in fluid communication with the carrier fluid duct 28 and/or analysis chamber and may be positioned downstream of the multi-port valves 26 for adding to the analysis chamber. The reagents may be introduced to the system via valve 52 thereby introducing a reagent to the plating bath sample to form a plating bath/reagent mixture that passes to the analysis chamber 12. For this purpose the appropriate valves 51, 52 and 53 may be operated several times to inject a required amount of reagent for mixing with the plating bath sample. Flow then continues to take the sample/reagent mixture to the analysis chamber 12. Notably, there is no limit to the number of reagent containers that may be connected to the carrier fluid duct 28 and/or analysis chamber 12.

Transference of the reagents, carrier fluid and/or primary electrolyte into the carrier fluid duct or analysis chamber typically comprises an electrically actuated syringe pump that dispenses a specific volume per stroke. However, analysis systems that require more than the typical transference volume of 5 ml of liquid take significantly longer due to the wait period associated with the syringe pump refilling. Refilling of the analysis chamber for each new sample analysis may require a significant volume of primary electrolyte and thus increase the time between each sample analysis. Thus, the present invention further comprises a transference syringe comprising a larger transference volume thereby decreasing the time required to refill the analysis chamber and/or to transferred reagents.

Figure 5:
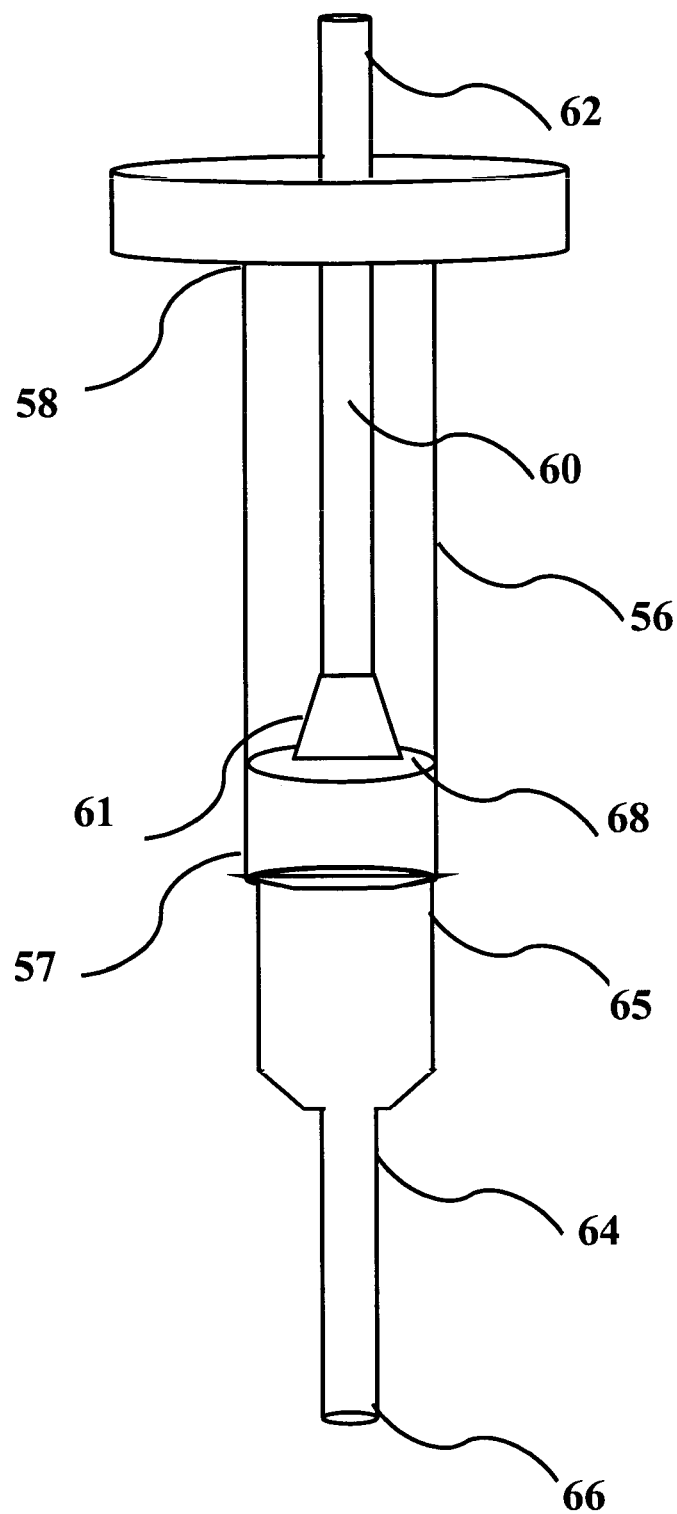
FIG. 5 illustrates a liquid transference syringe for accurately transferring a larger volume of reagents, carrier liquid and electrolytes.

As shown in FIG. 5, a transferring syringe of the present invention comprises a cylindrical housing 56 sized to accurately transfer about 10 to 20 ml of transferable liquid per stroke, wherein the cylindrical housing has an open first end 57 and a closed second end 58. Positioned and slidably mounted within the cylindrical housing is a cylindrical plunger rod 60 having a first and second end, 61 and 62, respectively. The second end 62 of the plunger rod extends through the closed second end of the housing 58. The syringe pump further comprises a tip comprising a body portion 64 comprising a central bore therethrough wherein a first end 65 of the tip is connected to the first end of the cylindrical housing. The second end 66 has a smaller bore diameter sized to reduce back pressure when filling and the formation of irreproducible droplets at the second end of the tip. More preferably the tip bore diameter is from about 0.5 mm to about 2 mm.

Figure 6:
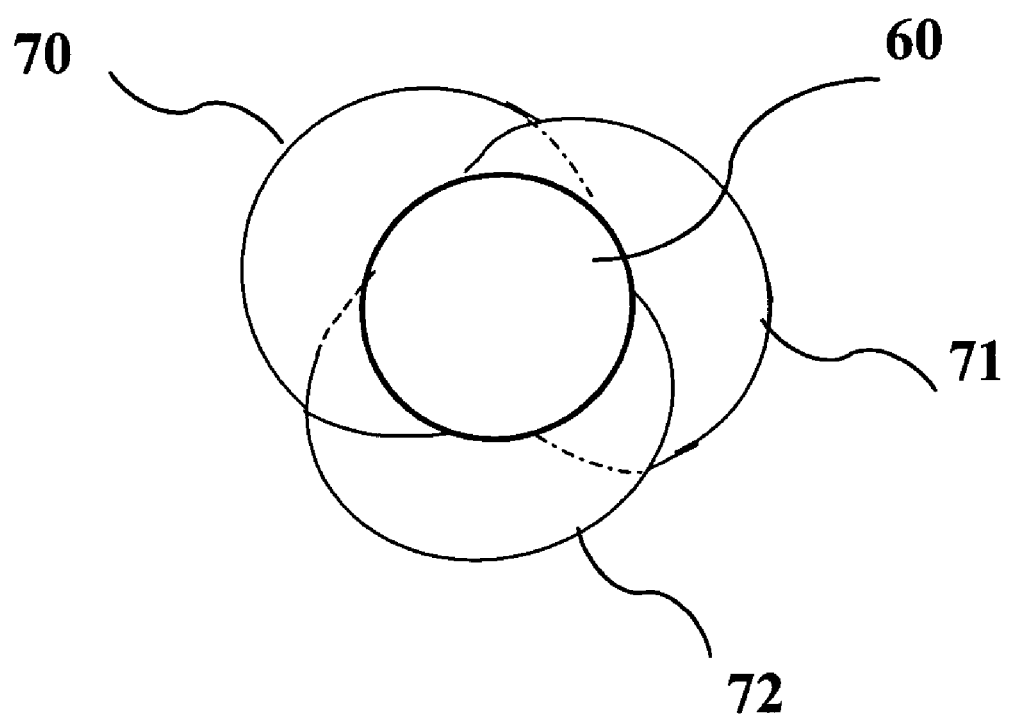
FIG. 6 illustrates a flexible sealing member showing three overlapping radial flaps.

Attached to the first end 61 of the plunger rod is a flexible sealing member 68 comprising three overlapping radial flaps that sealably form a liquid containing chamber 57 between the flexible sealing member and the second end of the tip for the holding a transferable liquid. The three overlapping radial flaps, 71, 72 and 73, as shown in FIG. 6, provide for a fluid tight seal that prevents any leakage from the liquid containing chamber into the area between the end of the cylindrical housing and the backside of flexible sealing member.

The sampling system of the present invention permits purging of the system between each sample analysis by flushing the system with an inert gas, followed by ejection of the gas and any remaining residue through the downstream drain outlet 36. Opening the valve 31 to the purging gas source 32 enables full flushing of the system. It should be noted that priming and/or flushing is not an essential intermediate step between successive samplings, which is advantageous if several samples aliquots are to be successively drawn from the same reservoir, for example to test for different analytes as discussed below relating to the second embodiment described in FIG. 2.

The system may be computer controlled with any chosen program which produces repeated valve operations, sample loadings, and reagent loadings in any chosen sequence, for example for on-stream monitoring or a complex series of analysis involving differing samples, differing analytes and differing reagents. The flow of flushing liquid, reagents and plating bath sample flows is controlled using solenoid valves connected to solid state relays. Solenoid valves are employed for automated reagent mixing and flow control that are communicatively connected to solid state relays that are computer controlled. The 2 way valves 44 and 3 way valves 51, 52 and 53 can be any commercially available valves, such as those made by Neptune Research Limited, Maplewood, N.J., USA. Additionally, the system may further comprise buffer coils 47 which are included if the analysis mode used in the analysis chamber comprises pH or high impedance ion-selective probes. Any type of buffer coil that is commercially available and well known to one skilled in the art may be used in the present invention A reagent or a mixture of reagents may be introduced into a non-reacting or inert carrier liquid and allowed to flow into the carrier fluid duct. Valve 52 may be used to introduce a carrier fluid and/or selected reagents thereby allowing for selected reagents, diluents or alternative carriers to enter the flow by replacing or mixing with the principal carrier. By operating valves 51 and 53 alternately it is possible to produce reagent mixtures in both carrier fluid ducts 28, and this technique is useful for reagent mixtures that would exhibit a short shelf life.

When the sample loop, having a precisely reproducible volume, is closed by switching the multi-port valve to the second position the plating bath sample in the sample loop is flowed into the carrier fluid duct. The precise reproducible volume is achieved by constructing the sample loops with specific a length of inert tubing having a known interior bore diameter. Preferably, the interior bore diameter of the sample loops and sampling duct is sufficient to include an inline flow sensor, if preferred. Further, the sample loop is of a length and diameter to ensure a quantity of the sample, which is sufficient for an accurate analysis. Notwithstanding the need to have a sufficient amount of fluid for an accurate analysis, the volume should be small enough to allow for considerable economy in the use of reagent and to reduce waste of expensive plating bath solutions. Preferably, the sample loops, hold a volume of from about 0.01 ml to about 10 ml of the plating bath sample before sending the sample to the analysis chamber, and more preferably from about 1 to about 3 mls. Further, the length of the tubing, as shown in FIG. 1, is of a sufficient length to connect the sample duct to the carrier fluid duct through the multi-port valve.

The analysis method conducted in the analysis chamber may include use of any suitable electrolysis or potentiometric analysis systems of a type well known to those skilled in the art. Preferred analysis methods are described in U.S. Pat. No. 6,495,011 or copending application U.S. patent application Ser. No. 09/690,770 filed on Oct. 17, 2000, the contents of which are hereby incorporated by reference herein for all purposes.

The present invention advantageously provides for the simultaneous analysis of a sample that has been flowed from the sample loop into the analysis chamber and the refilling of the sample loop with a new sample solution for subsequent analysis. The simultaneous rinsing of the sample duct and refilling of the sample loop while analysis is being conducted in the analysis chamber reduces the time required for multiple sampling. Further, the introduction of a sample into a flowing stream of liquid containing a reagent, within which the sample reacts while traveling to the analysis chamber, permits a high rate of sampling to be achieved.

Figure 2:
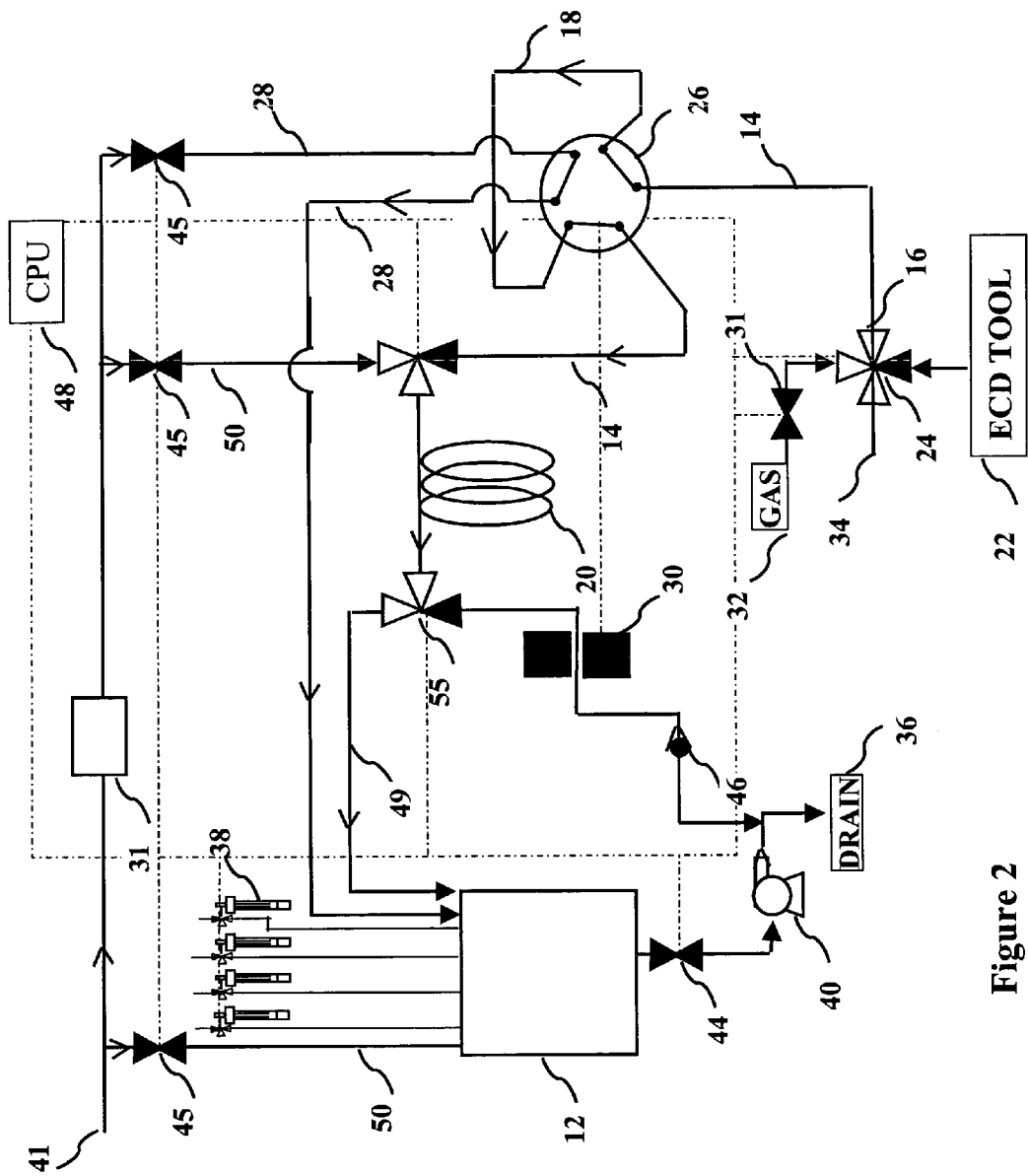
FIG. 2 illustrates another embodiment of the present invention for analysis of inorganic components in a plating bath solution.

Various modifications of the illustrated and described arrangement are possible within the scope of the present invention, and particular reference is made to FIG. 2 illustrating a sampling system applicable to the analysis of a plating bath comprising inorganic components such as copper, sulfuric acid and chloride as analyzed in the analysis chamber of the system.

A second embodiment comprises components as described in FIG. 1 and will be discussed with corresponding reference numbers. The second embodiment, as shown in FIG. 2, comprises a sampling duct 14 and two separate sample loops. The plating bath sample is drawn through the four-way valve 24, activated in the first mode, and then drawn into the sample duct 14 and through both sample loops 18 and 20. A sufficient amount of the plating bath solution is drawn into the system to flush any remaining previous sample from the sample duct 14 and effects its removal through drain outlet 36. During the analysis of the plating bath sample, the fluid sample can be directed through the first sample loop 18 or the second sample loop 20. In this embodiment, the second sample loop 20 holds a larger sample for analysis in the analysis chamber 12. During the analysis process, the samples retained in the sample loops 18 and 20 are both directed to the same analysis chamber, however at separate times via separate flow paths.

The sample in sample loop 18 is directed to the analysis chamber through the multi-port valve 26 that has been switched from the first position to the second position, thereby allowing the sample in the sample loop 18 to be redirected to the carrier fluid duct 28 for transference to the analysis chamber 12. In the alternative, the plating bath sample retained in sample loop 20 is directed through valve 55 and auxiliary sample duct 49 to the analysis chamber 12.

Thus, both sample loops are filled in the same filling process, but tested in separate and sequential testing procedures.

Multiple reagents reservoirs 38 are in fluid communication with the analysis chamber for adding reagents therein. Carrier fluid duct 28 and carrier lines 50 can be used for introducing deionized water into the analysis chamber. A flow regulator 31 positioned in the carrier fluid duct can regulate the flow of the carrier fluid.

The described sampling system advantageously has two separate sample loops, thereby providing for testing separate samples, using separate reagents to test for different components in two sequential testing procedures. This advantage is provided, as an option, because the contents in the two sample loops are flowed to the analysis chamber via separate flow paths.

Although the present invention has been described with reference to preferred embodiments, one skilled in the art will recognize that changes may be made in form and detail without departing from the spirit and scope of the invention. For instance, workers skilled in the art will appreciate that all of the various embodiments discussed herein may be employed with one or more of the other embodiments.

What is claimed is:

1. A sampling system for determining concentration of additives in a metal plating bath solution from an electrochemical processing tool, the system comprising:
   a) at least one analysis chamber,
   b) a sampling duct comprising a sampling inlet and a first and second sample loop for holding known amounts of a sample of the plating bath solution, wherein the sampling inlet is in fluid communication with the electrochemical processing tool for receiving a plating bath sample for analysis in the at least one analysis chamber,
   c) a four-way valve comprising a connection to a purging gas stream, a connection to the electrochemical processing tool for removal of a sample for analysis, a connection to a waste outlet and a connection to the sampling inlet for movement of the sample into the sampling duct;
   d) at least one actuatable multi-port valve positioned in fluid communication with at least one of the sample loops and in fluid communication with the sampling duct;
   e) at least one carrier fluid duct in fluid communication with the analysis chamber, wherein the carrier fluid duct and sampling duct are in fluid communication via the actuatable multi-port valve;
   f) a flow sensor in fluid communication with the sampling duct and positioned downstream from both of the sample loops, wherein the flow sensor measures a predetermined quantity of plating bath sample flowing through sample duct;
   g) a waste drain connected to the sampling duct and positioned downstream of the flow sensor and analysis chamber for removal of analyzed sample from the analysis chamber and excess sample removed from the sample duct; and
   h) a purging gas source in fluid communication with the four-way valve for introducing a purging gas into the sampling duct between successive sample analyses for flushing the sample, the analyzed sample or both from the system, or portions thereof, and into the waste drain.

2. The system according to claim 1, further comprising a valve control system for controlling the four-way valve to provide a first mode in which the plating bath sample is flowed from the processing tool into the sample duct, a second mode in which the plating bath sample from the processing tool is directed to the waste line, a third mode in which the purge gas is introduced to the sample duct to purge plating bath sample from the sample duct, and a fourth mode in which the purging gas is directed to the waste line without passing through the sample duct or first and second sampling loops.

3. The system according to claim 2, wherein the valve control system is communicatively connected to the flow sensor and the four-way valve, wherein the first mode of the four-way valve is turned off when the predetermined quantity of plating bath sample has flowed past the flow sensor.

4. The system according to claim 2, wherein the plating bath sample is purged from the sample duct by actuating the four-way valve and introducing a purging gas into the sample duct.

5. The system according to claim 2, wherein the at least one actuatable multi-port valve has a first and second position, and wherein the first position provides for the plating bath sample to flow through the sample duct and at least one of the sample loops and the second position provides for flowing the plating bath sample in the sample loop into the carrier fluid duct to the analysis chamber.

6. The system according to claim 5, wherein the actuatable multi-port valve is in the first position for purging the sample duct with the purging gas source.

7. The system according to claim 5, wherein the plating bath sample in at least one of the sample loops is flowed into the carrier fluid duct when the multi-port valve is actuated into the second position and the four-way valve is in the third mode wherein the purging gas source is introduced to the sample duct to purge plating bath sample from the sample duct thereby providing for simultaneously purging of the sample duct and analysis of plating bath sample in the analysis chamber.

8. The system according to claim 1, comprising at least two analysis chambers and two actuatable multi-port valves, one of said chambers and multi-port valves being in fluid contact with the first sample loop and the other chamber and multi-port valve being in fluid contact with the second sample loop.

9. The system according to claim 1, further comprising reagent containers for holding reagents that are introduced into the at least one analysis chamber.

10. The system according to claim 1, further comprising reagent containers for holding reagents that are introduced into the at least one analysis chamber and the carrier fluid duct.

11. The system according to claim 1, wherein each sample loop contains from about 1 ml to about 10 ml of plating bath sample.

12. The system according to claim 1 wherein the first sample loop contains a smaller volume of plating bath sample than the second sample loop and both sample loops fill at approximately the same time.

13. The system according to claim 12, wherein the smaller fluid amount of plating bath sample is introduced into the analysis chamber from the sample duct through the actuatable multi-port valve and the carrier fluid duct.

14. The system according to claim 12, further comprising an auxiliary sample duct in fluid communication with the sample duct and analysis chamber, wherein the plating bath sample contained in the second sample loop is introduced into the analysis chamber through the auxiliary sample duct.

15. The system according to claim 1, further comprising a drain pump in fluid communication with the analysis chamber to drain used analysis solution from the analysis chamber.

16. The system according to claim 1, further comprising a liquid transferring system for injecting a primary electrolyte into the analysis chamber.

17. The system according to claim 16, wherein the transferring system comprises an electrolyte fluid and a transfer device adapted to transfer a measured amount of electrolyte to the analysis chamber.

18. The system according to claim 17, wherein the transfer device adapted to transfer a measured amount of the liquid comprises a syringe pump.

19. The system according to claim 18, wherein the syringe pump comprises:
   a) a cylindrical housing sized to transfer at least 10 ml of liquid, wherein the cylindrical housing has an open first end and a closed second end;
   b) a cylindrical plunger rod having a first and second end and slidably mounted within the cylindrical housing, wherein the second end of the plunger rod extends through the closed second end of the housing;
   c) a tip comprising a body portion having a first and second tip end and a central bore therethrough wherein the first end of the tip is connected to the first end of the cylindrical housing, and wherein the second end has a bore diameter sized to reduce back pressure when filling and reduce the formation of irreproducible droplets at the second end of the tip; and
   d) a flexible sealing member connected to the first end of the plunger rod, wherein the flexible sealing member comprises three overlapping radial flaps to form a sealed chamber between the flexible sealing member and the second end of the tip, and wherein the sealed chamber holds a transferable liquid.

20. A system for determining additives in a metal plating bath in an electrochemical processing tool, the system comprising:
   a) at least one analysis chamber
   b) a sampling duct comprising a sampling inlet and at least one sample loop for holding a known amount of sample positioned upstream from the sample inlet, wherein the sampling duct is in fluid communication with the processing tool for receiving a plating bath sample for analysis in the at least one analysis chamber,
   c) an inlet four-way valve positioned before the sampling duct to received the plating bath sample from the electrochemical processing tool and introduce same to the sampling duct;
   d) at least one carrier fluid duct in fluid communication with the analysis chamber and sampling duct;
   e) at least one actuatable multi-port valve positioned in fluid communication with the at least one sample loop and in fluid communication with the sampling duct and carrier fluid duct, wherein the at least one actuatable multi-port valve has a first and second position, and wherein the first position provides a flow for flowing the plating bath sample through the sampling duct and into the at least one sample loop and the second position provides a flow path for flowing the plating bath sample from the at least one sample loop to the carrier fluid duct;
   f) a flow sensor in fluid communication with the sampling duct and positioned downstream from the at least one sample loop wherein the flow sensor measures a predetermined quantity of plating bath sample flowing through sample duct and then triggers the actuation of the multi-port valve into the second position;
   g) a purging gas source connected to the four-way valve for introducing a purging gas into the sampling duct to purge plating bath sample from the whole or a portion of the system;
   h) a waste line in fluid communication with the four-way valve, wherein plating bath solution is transferred from the processing tool through the four-way valve to the waste line; and
   i) a valve control system for controlling the inlet four-way valve to provide a first mode in which the plating bath sample is flowed from the processing tool into the sample duct, a second mode in which the plating bath sample from the processing tool is directed to the waste line, a third mode in which the purge gas source is introduced to the sample duct to purge plating bath sample from the sample duct, and a fourth mode in which the purging gas source is directed to the waste line without passing through the sample duct or sampling loops.

21. The system according to claim 20, which comprises two sample loops, wherein the first sample loop retains a smaller volume of plating bath sample than the second sample loop and both sample loops are filled in the same, filling process.

22. The system according to claim 21, wherein the plating bath samples in the sample loops are sequentially moved to the analysis chamber via separate flow paths.

23. The system according to claim 20, wherein analysis of a plating bath sample is conducted simultaneously with the refilling of the at least one sample loop.

24. The system of claim 1 wherein there is a single actuatable multi-port valve and said single actuatable multi-port valve is in fluid communication with both sample loops and the sampling duct.

25. The sampling system of claim 24 wherein the actuatable multi-port valve has at least two positions, a first position providing for the plating bath sample to flow through the sample duct and the first sample loop and a second position providing for the plating bath sample to flow through the sample duct and the second sample loop.

26. The sampling system of claim 25 wherein when said multi-port valve is in the first position, the second sample loop is in fluid communication with the carrier fluid duct and when said multi-port valve is in the second position., the first sample loop is in fluid communication with the carrier fluid duct.

27. The sampling system of claim 24 wherein the actuatable multi-port valve has four positions, a first position providing for the plating bath sample to flow through the sample duct and the first sample loop, as second position providing for the plating bath sample to flow through the sample duct and the second sample loop, a third position providing for flowing the sample in the first sample loop into the carrier fluid duct to the analysis chamber and a fourth position providing for flowing the sample in the second sample loop into the carrier fluid duct to the analysis chamber.

28. The system of claim 1 comprising two actuatable multi-port valves, one in fluid communication with the sampling duct and the first sample loop and the second in fluid communication with the sampling duct and the second sample loop.

* * * * *